United States Patent [19]

Krüger

[11] 4,358,596
[45] Nov. 9, 1982

[54] PROCESS FOR THE PREPARATION OF 1,2,3-THIADIAZOL-5-YL UREAS

[75] Inventor: Hans-Rudolf Krüger, Berlin, Fed. Rep. of Germany

[73] Assignee: Schering AG, Berlin and Bergkamen, Fed. Rep. of Germany

[21] Appl. No.: 226,899

[22] Filed: Jan. 21, 1981

Related U.S. Application Data

[63] Continuation of Ser. No. 89,106, Oct. 29, 1979, abandoned.

[30] Foreign Application Priority Data

Nov. 3, 1978 [DE] Fed. Rep. of Germany ....... 2848330

[51] Int. Cl.³ ................. C07D 285/06; C07D 413/12; C07D 417/12
[52] U.S. Cl. ................................. 548/127; 544/134; 544/327; 544/331; 546/209; 546/277
[58] Field of Search ............... 548/127; 544/134, 324, 544/327, 331; 546/209, 277

[56] References Cited

PUBLICATIONS

Yale, Chem. Reviews, vol. 33, pp. 242–249 (1943).
Renfrow et al., J. Am. Chem. Soc., vol. 59, pp. 2308–2314 (1937).

*Primary Examiner*—Alton D. Rollins
*Attorney, Agent, or Firm*—Michael J. Striker

[57] ABSTRACT

A process for the preparation of 1,2,3-thiadiazol-5-yl ureas of the general formula

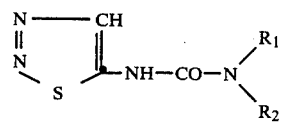

I in which a 1,2,3-thiadiazol-5-carbohydroxam acid derivative of the formula

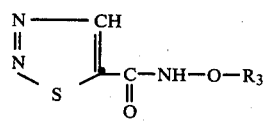

II is dissolved in an inert organic solvent with an acid halide of the formula

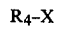

III $R_4-X$ to form an acylated derivative which then reacts with an amine of the formula

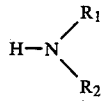

V to form the desired product.

13 Claims, No Drawings

PROCESS FOR THE PREPARATION OF 1,2,3-THIADIAZOL-5-YL UREAS

This is a continuation of application Ser. No. 089,106, filed Oct. 29, 1979, now abandoned.

The invention concerns a novel process for the preparation of 1,2,3-thiadiazol-5-yl ureas, which find use as plant protection agents on account of their herbicidal and growth regulation properties.

Processes for the preparation of ureas of this type are already known. (DE-OS 221 46 32, DE-OS 263 69 94) All of these processes have nonetheless the great disadvantage, that they use 5-amino-1,2,3-thiadiazole as starting material, a substance which is not easily prepared and also not totally safe.

It is an object of the invention to provide a process which allows for a problem-free preparation of 1,2,3-thiadiazol-5-yl ureas with high yields and with few process steps, and which also permits a technical-scale preparation of these substance classes without the isolation of intermediates which might require consideration with respect to technical safety.

This object is achieved through a process for the preparation of 1,2,3-thiadiazol-5-yl ureas of the general formula

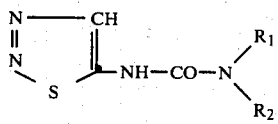   I in which $R_1$ is hydrogen or if desired an alkyl which may be interrupted one or more times by a sulfur or oxygen atom;

$R_2$ is alkyl which may be interrupted one or more times by sulfur or oxygen atoms, cycloalkyl residues optionally substituted by one or more alkyl groups, and aromatic hydrocarbon residue optionally substituted by one or more of alkyl, halogen, alkylthio, alkoxy, trifluoromethyl and nitro, a heterocyclic hydrocarbon containing at least one nitrogen atom and optionally substituted, or $R_1$ and $R_2$ together with the nitrogen atom from a morpholino-, piperidino- or pyrrolidino-group, which process is characterized in that a 1,2,3-thiadiazol-5-carbohydroxam acid derivative of the formula

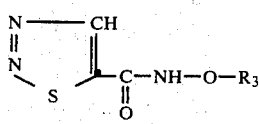   II is dissolved in an inert organic solvent with an acid halide of the formula

   III in the presence of acid-binding agents to form acylated 1,2,3-thiadiazol-5-carbohydroxam acid derivatives of the formula

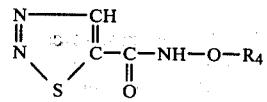   IV which is reacted with an amine of the formula

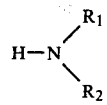   V and the reaction product then isolated in conventional manner, in which $R_1$ and $R_2$ have the above meanings, $R_3$ is hydrogen or a univalent metal equivalent, preferably a sodium, potassium or lithium atom, $R_4$ an optionally substituted $C_1$–$C_4$ alkylcarbonyl residue, a $C_1$–$C_4$ alkoxycarbonyl residue, an optionally substituted benzoyl residue, or an optionally substituted aryl- or alkylsulfonyl residue and X is halogen, preferably chlorine.

As residues which are included within general formula I are those in which $R_1$ is hydrogen or $C_1$–$C_4$ alkyl, such as methyl, ethyl, propyl, isopropyl or butyl, $R_2$ is $C_1$–$C_4$ alkyl, such as methyl, ethyl, propyl, isopropyl or butyl, $C_5$–$C_8$ cycloalkyl, such as cyclopentyl or cyclohexyl, methyl-$C_5$–$C_8$ cycloalkyl, such as methylcyclohexyl, phenyl, halophenyl, such as 4-chlorophenyl, $C_1$–$C_4$ alkylphenyl, such as 4-methylphenyl, $C_1$–$C_4$ alkoxyphenyl, such as 4-methoxyphenyl, nitrophenyl, trifluoromethylphenyl, pyridyl or pyrimidyl.

As residues included within the scope of $R_4$ should be understood for example as $C_1$–$C_4$-alkylcarbonyl residues acetyl, propionyl, butyryl, isobutyryl, valeryl, isovaleryl or pivaloyl, as substituted $C_1$–$C_4$-alkylcarbonyl residues chloroacetyl, dichloroacetyl, trichloroacetyl, methoxyacetyl, 2-chloropropionyl, 3-chloropropionyl, 4-chlorobutyryl, bromoacetyl, 2-bromopropionyl or 3-bromopropionyl, as $C_1$–$C_4$-alkoxycarbonyl residues methoxycarbonyl, ethoxycarbonyl, propoxycarbonyl, isopropoxycarbonyl, butoxycarbonyl, tert.-butoxycarbonyl, isobutoxycarbonyl or sec.-butoxycarbonyl, as optionally substituted benzoyl residues, benzoyl, 4-chlorobenzoyl, 3-chlorobenzoyl, 2-chlorobenzoyl, 4-methoxybenzoyl, 3-methoxybenzoyl, 2-methoxybenzoyl, 4-methylbenzoyl, 3-methylbenzoyl, 2-methylbenzoyl or as optionally substituted aryl, respectively alkylsulfonyl residues phenylsulfonyl, 4-tolylsulfonyl, 4-bromophenylsulfonyl, 4-chlorophenylsulfonyl, naphthyl-2-sulfonyl, 4-nitrophenylsulfonyl, 2-nitrophenylsulfonyl, 4-fluorophenylsulfonyl, methylsulfonyl, ethylsulfonyl or benzylsulfonyl.

Particular embodiments of the invention include that the reaction takes place at temperatures between about $-20°$ C. to $100°$ C., preferably at temperatures from $0°$ C. to $50°$ C., that equimolar amounts of the hydroxam acid derivative of general formula II, the acid halide of general formula II as well as of amine of general formula V are employed, that the reaction of the acylated hydroxam acid derivative of general formula IV with the amine of general formula V takes place in a single step, that the reaction of the 1,2,3-thiadiazol-5-carboxam acid of formula II with the acid halide of formula II and the amine of formula V takes place in a single step, and that 1,2,3-thiadiazol-5-carbohydroxam acids of formula II are used, which are prepared according to known processes and are not isolated from the reaction mixtures, through which it is also possible to have a continuous process.

The preparation of the 1,2,3-thiadiazole-5-carboxylic acid needed for the formation of the carboxylic acid is known from the literature, as is the use of 1,2,3-thiadiazol-5-carboxylic acid chloride and the 1,2,3-thiadiazol-5-carboxylic acid ethyl ester.

The until now unknown 1,2,3-thiadiazol-5-carbohydroxam acids as well as salts thereof of the formula II

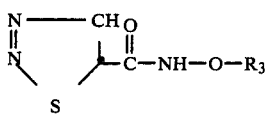  II can be prepared according to the following processes which are known, in which (a) 1,2,3-thiadiazol-5-carboxylic acid esters of the general formula

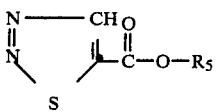  VI are reacted with hydroxylamine of the formula

  VII if desired in the presence of inorganic bases, such as oxides, hydroxides or carbonates and alcoholates of the alkali or alkali earth metals, if desired, dissolved in polar organic solvents; or (b) 1,2,3-thiadiazol-5-carboxylic acid halides of the general formula

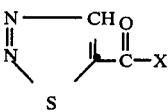  VIII are reacted with hydroxylamine of the formula

  VII dissolved in inert solvents in the presence of acid-binding agents, in which $R_5$ is a $C_1$–$C_6$ alkyl residue and $R_3$ and X have the above meanings.

The inventive process thus uses easily accessible starting materials and makes possible a technically simple and safe preparation of the desired reaction products.

It is of great technical advantage, that neither the acylated carbohydroxam acid derivative IV nor the 1,2,3-thiadiazol-5-yl-isocyanate formed needs to be isolated from the reaction mixture in which it is prepared. Moreover, the carbohydroxam acid derivative II can, in a one-pot reaction, be reacted directly with the acid halide III and the amine V in the presence of acid acceptors.

It is also of advantage, that the raw carbohydroxam acids or their salts II as well as the raw solution can be used.

It is particularly surprizing, that in this type of reaction the desired reaction product is predominantly produced and not as would be expected the amide of the acid used for acylation of the carbohydroxam acid. In addition, the yields have surprizingly been very high.

The reaction of the 1,2,3-thiadiazol-5-carbohydroxam acid of formula II, preferably in the form of the raw product, to 1,2,3-thiadiazol-5-yl ureas of formula I occurs through a solution dissociation via the step of the acylated carbohydroxam acid of formula IV, which as a rule it is not necessary to isolate, as well as over the step of the 1,2,3-thiadiazol-5-yl isocyanate which as well as a rule is not separately isolated, but instead generated in situ and reacted immediately with the amine of formula V.

The reaction takes place at temperatures between $-20°$ C. and $100°$ C., preferably between $0°$ C. and $50°$ C. The carrying out of the inventive process can for example take place, by a process in which one reacts a raw solution of the hydroxam acid in mixture with an equimolar amount of the acid halides in an inert solvent, then mixed with a mixture of equimolar amounts of amine and acid-binders in an inert solvent, in which the hydroxam acid/acid halide mixture is first mixed with the acid-binder and then with the amine; in which one first reacts the hydroxam acid/acid binder mixture with the acid halide and then with the amine; or also in a process in which one adds the acid halide to a mixture of the hydroxam acid, acid-binder and amine.

Through the use of the hydroxam acid salt the use of acid-binders is also eliminated.

As solvents which are inert to the reactants or as liquids for forming a suspension of the reactants may be mentioned the following: aliphatic and aromatic hydrocarbons such as cyclohexane, heptane, ligroin, benzene, chlorobenzene, toluene and xylene, ethers such as diethyl ether, dioxane, tetrahydrofuran and diisopropyl ether, esters such as ethyl acetate and malonic esters, ketones such as acetone, methyl isobutyl ketone, isophorone and cyclohexanone, halogenated hydrocarbons such as methylene chloride, chloroform and carbon tetrachloride, carboxylic acid amides such as dimethyl formamide, or sulfoxides such as dimethyl sulfoxide.

As acid-binders are suitable organic bases, such as triethylamine, N,N-dimethylaniline and pyridine bases or inorganic acids, such as oxides, hydroxides and carbonates of the earth alkali and alkali metals. Liquid bases such as pyridine can simultaneously be used as solvent.

After the reaction, the reaction mixture is worked up in conventional manner, for example through filtration of the inorganic salts and a subsequent distillation of the solvent at normal or reduced pressure, precipitation with water or in most cases through simple filtration of the desired reaction product and a subsequent washing out of the inorganic salts with water.

One obtains in this manner 1,2,3-thiadiazol-5-yl ureas in exceptionally pure form and in very good yields, which require for subsequent uses no subsequent purification operations.

Separation problems, such as arise in the reaction of 5-amino-1,2,3-thiadiazoles with isocyanates, with respect to the symmetric ureas which fall out as side products, are thus avoided.

The following examples serve to illustrate the carrying out of the inventive process.

EXAMPLE 1

Preparation of 1-phenyl-3-(1,2,3-thiadiazol-5-yl) urea from 1,2,3-thiadiazol-5-carbohydroxam acid In a three-necked 500 ml round bottom flask with a stirrer, thermometer and drying tube, 14.5 g (0.1 Mol) of 1,2,3-thiadiazol-5-carbohydroxam acid in 200 ml tetrahydrofuran is suspended and at 4° C. reacted with 19.0 g (0.1 Mol) p-toluenesulfonic acid chloride, dissolved in 50 ml tetrahydrofuran.

To this is added dropwise over 10 minutes a mixture of 27.8 ml (0.2 Mol) triethylamine and 9.1 ml (0.1 Mol) aniline in 50 ml tetrahydrofuran. The interior temperature is held between about 3° and 6° C. A light yellow reaction mixture is thereby formed. This is stirred for one hour at 5% C and one hour at room temperature; thereby rises the interior temperature shortly to 28° C. After standing overnight, the mixture is thoroughly concentrated under vacuum at 40° C.; the residue is mixed with 800 ml ice water; after a little scratching one obtains solid white crystals, which are collected, washed with water and dried to constant weight under vacuum at room temperature.

Yield: 14.9 g=67.7% of theory
M.P.: 208°–210° C. (decomposition)
LC: $R_f$=0.25 (solvent-ethyl acetate)

EXAMPLE 2

Preparation of 1-phenyl-3-(1,2,3-thiadiazol-5-yl) urea from 1,2,3-thiadiazol-5-carbohydroxam acid In a three-neck 100 ml round bottom flask with a stirrer, thermometer and drying tube 1.45 g (0.01 Mol) 1,2,3-thiadiazol-5-carbohydroxam acid in 20 ml tetrahydrofuran is suspended and then reacted with a mixture of 2.8 ml (0.02 Mol) triethylamine and 0.91 ml (0.01 Mol) aniline. To this is added dropwise over 10 minutes at 4° C. a solution of 1.9 g (0.01 Mol) p-toluenesulfonic acid chloride in 5 ml tetrahydrofuran. This is stirred for one hour at 5° C. and one hour at room temperature; the interior temperature shortly rises to 27° C. After standing overnight, the mixture is concentrated under vacuum at 40° C.; the residue is mixed with 80 ml ice water; the crystals are collected, washed with water and dried under vacuum to a constant weight at room temperature.

Yield: 1.5 g=68.1% of theory
M.P.: 208°–210° C. (decomposition)

The following examples illustrate the preparation of the starting material.

EXAMPLE 3

Preparation of 1,2,3-thiadiazol-5-carbohydroxam acid

In a three-neck 250 ml round bottom flask with stirrer, thermometer, reflux condenser and drying tube, 15.65 g (0.225 Mol) pulverized hydroxylamine hydrochloride is thoroughly dissolved in 90 ml methanol and at 20° C. is reacted with a methanolic solution of potassium hydroxide, prepared from 14.0 g (about 0.225 Mol) potassium hydroxide powder (ca. 90%) and 60 ml methanol. The mixture is stirred for another 30 minutes at room temperature, the precipitated potassium chloride is collected and the filtrate is reacted in an apparatus as described above with 23.8 g (0.15 Mol) 1,2,3-thiadiazol-5-carboxylic acid ethyl ester at room temperature. The reaction solution turns yellow immediately. After standing for two days at room temperature the mixture is concentrated under vacuum at 40° C.; the yellow mixture residue is brought to full crystallization in 100 ml acetonitrile; the product is isolated, washed with about 20 ml acetonitrile and dried to constant weight under vacuum at room temperature. One obtains a lightly yellow crystallisate.

Yield: 20.0 g=91.8% of theory
M.P.: 109°–111° C. (decomposition)
LC: $R_f$=0.36 (solvent-ethyl acetate)
Probe recrystallized from acetonitrile
M.P.: 134° C. (decomposition)

EXAMPLE 4

Preparation of 1,2,3-thiadiazol-5-carbohydroxam acid potassium salt

In a three-necked flask with stirrer, thermometer and drying tube 13.9 g (0.2 Mol) hydroxylamine hydrochloride in 100 ml methanol is suspended and reacted with a solution of 19.6 g (0.35 Mol) potassium hydroxide in 50 ml methanol at 15° to 20° C. One stirs the mixture for an hour at room temperature, collects the precipitated potassium chloride and reacts the filtrate at room temperature with 23.8 g (0.15 Mol) 1,2,3-thiadiazol-5-carboxylic acid ethyl ester. After standing for three days at room temperature, the precipitated yellow crystals are collected, washed with a little isopropanol and dried at room temperature under vacuum.

Yield: 22.3%=81.4% of theory
M.P.: 215° C. (decomposition)

The compounds prepared according to the inventive process can be used for example as plant growth regulators and as defoliants.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process for the preparation of 1,2,3-thiadiazol-5-yl ureas of the formula

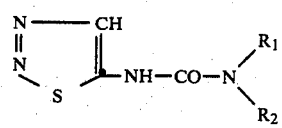                                       I where $R_1$ is hydrogen or $C_1$–$C_4$-alkyl; $R_2$ is $C_1$–$C_4$-alkyl, $C_5$–$C_8$-cycloalkyl, $C_5$–$C_8$-cycloalkyl substituted by one or more alkyl groups, pyridyl, pyrimidyl, phenyl, or phenyl substituted by one or more residues selected from the group consisting of alkyl, halogen, alkylthio, alkoxy, trifluoromethyl and nitro, or in which $R_1$ and $R_2$ with the N-atom form a morpholino-, piperidino- or pyrrolidino-group, comprising reacting a compound of the formula

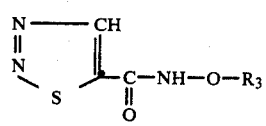                                       II with an acid halide of the formula

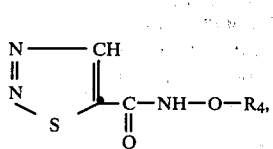   III dissolved in an inert organic solvent in the presence of acid binding agents to form acylated 1,2,3-thiadiazol-5-carbohydroxam acid derivatives of the formula

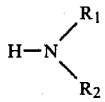   IV reacting this compound with an amine of the general formula

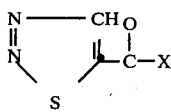   V and isolating the product, in which $R_1$ and $R_2$ are as defined above, $R_3$ is hydrogen or a univalent metal atom, $R_4$ is $C_1$–$C_4$-alkylcarbonyl, $C_1$–$C_4$-alkylcarbonyl substituted by one or more halogen atoms, $C_1$–$C_4$-alkoxycarbonyl, benzoyl, benzoyl substituted by halogen, methyl or methoxy, phenyl sulfonyl, phenylsulfonyl substituted by halogen, methyl or nitro, alkylsulfonyl or alkylsulfonyl substituted by alkyl or benzyl, and X is a halogen atom.

2. The process of claim 1, wherein $R_3$ is a sodium, potassium or lithium atom.

3. The process of claim 1, wherein X is a chlorine atom.

4. The process of claim 1, wherein the reaction is carried out at between about 0° C. and 50° C.

5. A process as defined in claim 1, wherein the reaction is carried out between about −20° C. and 100° C.

6. A process as defined in claim 1, wherein equimolar amounts of the hydroxam acid derivative salt of formula II, the acid halide of formula III and the amine of formula V are reacted together.

7. A process as defined in claim 1, wherein the reaction of the acylated hydroxam acid derivatives of general formula IV with the amine of formula V is carried out in a single step.

8. A process as described in claim 1, wherein the reaction of the 1,2,3-thiadiazol-5-carbohydroxam acid of formula II with the acid halide of formula III and the amine of formula V is carried out in a single step.

9. A process as defined in claim 1, wherein the 1,2,3-thiadiazol-5-carbohydroxam acid of formula II is used as prepared and not isolated from the preparation reaction mixture.

10. A process as defined in claim 9, wherein 1,2,3-thiadiazol-5-carbohydroxam acid of the formula II is prepared by reacting 1,2,3-thiadiazol-5-carboxylic acid ester of the formula

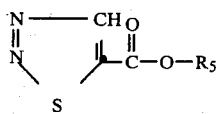   VI with a hydroxylamine of the formula $H_2N$—OH   VII if desired in the presence of inorganic bases and if desired dissolved in a polar organic solvent, wherein $R_5$ is a $C_1$–$C_6$ alkyl residue.

11. A process as defined in claim 9, wherein 1,2,3-thiadiazol-5-carbohydroxam acid of the formula II is prepared by reacting 1,2,3-thiadiazol-5-carboxylic acid halide of formula

   VIII with hydroxylamine of the formula $H_2N$—OH   VII dissolved in inert solvent in the presence of acid-binding agents, wherein $R_3$ and X are as defined above.

12. A process as defined in claim 1, wherein $R_4$ is $C_1$–$C_4$-alkylcarbonyl, chloroacetyl, dichloroacetyl, trichloroacetyl, methoxyacetyl, 2-chloropropionyl, 3-chloropropionyl, 4-chlorobutyryl, bromoacetyl, 2-bromopropionyl, 3-bromopropionyl, $C_1$–$C_4$-alkoxycarbonyl, benzoyl, 4-chlorobenzoyl, 3-chlorobenzoyl, 2-chlorobenzoyl, 4-methoxybenzoyl, 3-methoxybenzoyl, 2-methoxybenzoyl, 4-methoxybenzoyl, 3-methylbenzoyl, 2-methylbenzoyl, phenylsulfonyl, 4-tolylsulfonyl, 4-bromophenylsulfonyl, 4-chlorophenylsulfonyl, 2-nitrophenylsulfonyl, 4-fluorophenylsulfonyl, methylsulfonyl, ethylsulfonyl or benzylsulfonyl.

13. A process as defined in claim 1 for the preparation of 1-phenyl-3-(1,2,3-thiadiazol-5-yl) urea.

* * * * *